US005233980A

United States Patent [19]

Mestas et al.

[11] Patent Number: 5,233,980

[45] Date of Patent: Aug. 10, 1993

[54] APPARATUS AND METHOD FOR GENERATING SHOCKWAVES FOR THE DESTRUCTION OF TARGETS, PARTICULARLY IN EXTRACORPOREAL LITHOTRIPSY

[75] Inventors: Jean-Louis Mestas, Chassieu; Dominique Cathignol, Genas; Bernard Lacruche, Lyons, all of France

[73] Assignees: Technomed International Societe Anonyme, Paris; INSERM, Paris Cedex, both of France

[21] Appl. No.: 460,119

[22] PCT Filed: Nov. 15, 1988

[86] PCT No.: PCT/FR88/00560

§ 371 Date: May 15, 1990

§ 102(e) Date: May 15, 1990

[87] PCT Pub. No.: WO89/05026

PCT Pub. Date: Jun. 1, 1989

[30] Foreign Application Priority Data

Nov. 16, 1987 [FR] France ................................ 87 15799

[51] Int. Cl.[5] ............................................ A61B 17/22

[52] U.S. Cl. ............................................ 128/24 EL

[58] Field of Search ..................... 128/24 EL, 24 AA; 367/147

[56] References Cited

U.S. PATENT DOCUMENTS 2,559,227 7/1951 Rieber .
4,915,094 4/1990 Lacruche .

FOREIGN PATENT DOCUMENTS 0108190 6/1983 European Pat. Off. .
124686 2/1984 European Pat. Off. .
3150430 7/1983 Fed. Rep. of Germany .
2247195 10/1974 France .
2240795 3/1975 France .
2593382 1/1986 France .
2598074 4/1986 France .
2600520 6/1986 France .

OTHER PUBLICATIONS

Biomedizinische Technik, vol. 22, No. 7–8, Jul.–Aug. 1977, B. Forssmann et al., "Eine Methode zur Beruhrungsfreien Zertrummerung von Nierensteinen durch Stosswellen", especially pp. 164–169; p. 166, lines 16–37; FIG. 2.

IEEE 1977 Ultrasonics Symposium Proceedings, Phoenix, Ariz., /Oct. 26–28, 1977, editors J. de Klerk et al., IEEE, Inc. (New York, US), H. Finkler et al., "Experiments with Focussing Devices for the Touchless Destruction of Kidney Stones," especially pp. 157–160 and p. 157 Focussing Devices.

Forsmann et al., "Extra Corporeal Shock Wave Lithotripsy", Editor Ch. Chaussy, Munich, 1982, pp. 1–112.

*Primary Examiner*—Lee S. Cohen
*Assistant Examiner*—K. M. Pfaffle
*Attorney, Agent, or Firm*—Cohen, Pontani, Lieberman, Pavane

[57] ABSTRACT

The invention relates to a process for manufacturing a device generating shockwaves which are only slightly, if at all, felt be the patients.

This shockwave generating device comprises a truncated ellipsoidal reflector (12) which has a ratio (b)/(a) greater than 0.69, and preferably between 0.60 and 0.85 and a connection (14) supplying electric current to the electrodes (6, 8), which connection comprises a capacitor (18) having a capacitance less than or equal to 500 nanofarads.

The result is a reduction of the energy density at skin level of the emitted shockwaves which are only slightly, if at all, felt by the patients, thus permitting a treatment without anaesthesia.

35 Claims, 2 Drawing Sheets

Figure 1:
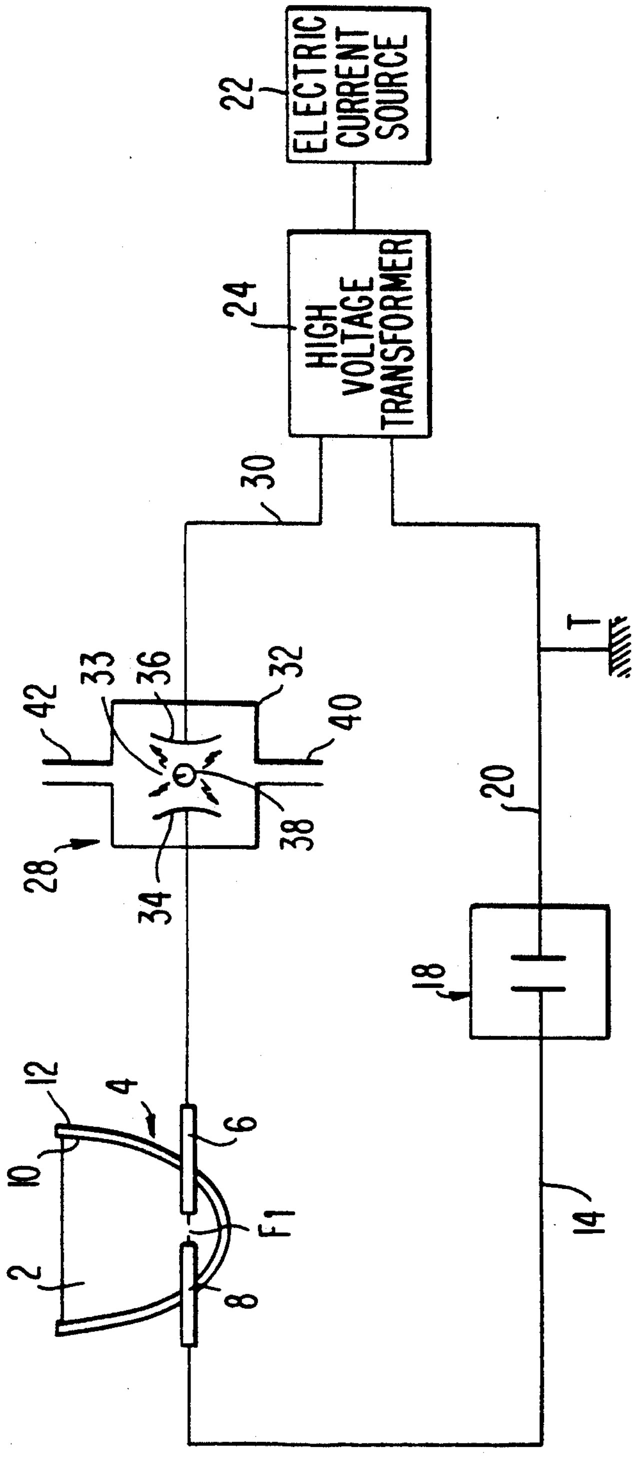

APPARATUS AND METHOD FOR GENERATING SHOCKWAVES FOR THE DESTRUCTION OF TARGETS, PARTICULARLY IN EXTRACORPOREAL LITHOTRIPSY

The present invention relates essentially to a device generating shockwaves for the touchless destruction of targets, preferably constituted by concretions, such as kidney lithiases or cholelithiases, said shockwaves being felt only slightly, if at all, by the patients, thus permitting a treatment without anaesthesia, and to a truncated ellipsoidal reflector and a shockwave generating apparatus for applying said process.

An apparatus is known from U.S. Pat. No. 2,559,227 to RIEBER, for generating high frequency shockwaves into a liquid for touchless destruction of targets which is herein incorporated by reference. Said apparatus comprises a shockwave generator formed by a truncated reflector 80 comprising a cavity 81 constituting a chamber of same truncated ellipsoidal shape for reflecting the shockwaves. One of the two focus points of the ellipsoid is situated inside the chamber opposite the truncated part, said chamber being filled with a shockwave transmitting liquid 83, e.g. an oil. Said chamber is closed by a membrane designated by the reference 37.

The current shockwave generating device conventionally comprises two electrodes 12, 13 disposed at least partly inside the chamber 81, both electrodes being so arranged as to generate a discharge or electric arc to the focus 14 situated in the chamber opposite the truncated part.

Means 10, 11 are also provided for selectively and instantaneously delivering a voltage to the two electrodes 12, 13 thereby causing the discharge or electric arc between the electrodes thus generating shockwaves in the liquid contained in the chamber.

In the RIEBER document, an electric power generator 10 is provided, particularly a battery 34, which selectively supplies a transformer 33 and a capacitor 11. This capacitor can be charged up to a voltage of 15,000 volts and have a capacitance of 1 microfarad in order to generate the electric arc or discharge between the electrodes in selective manner at preset intervals.

It is indicated that the value of the applied voltage and the size of the capacitor are dependent on the nature of the proposed use, whether the object is to destroy tissues or simply to stimulate them.

This apparatus is used in the medical field, particularly for destroying tissues. This apparatus can also be used for exploration purposes or for stimulating various parts of the nervous system.

This apparatus can also be used for extra-corporeal lithotripsy.

Document FR-A-2 247 195 also describes a similar apparatus in which the liquid is constituted by water.

Up to now, the technological improvements which have been brought to the RIEBER apparatus concern in particular the design of the electrodes (EP-A-0 124 686 or FR-A-2 593 382 or FR-A-2 598 074).

Other improvements concern the electrical power supply connection (FR-86 09 474).

No prior research had been made towards improving the patients' treatment conditions.

The present inventors have found that the treatment with shockwaves of patients suffering from lithiases could be carried out with this method without a local or general anesthesia.

Once the patient has been prepared and placed under anesthesia a constant watch has to be kept until the end of the treatment.

It is a fact that an anesthesia presents a definite risk for the patient, and its administration requires an important and expensive equipment as well as a highly qualified personnel to operate the necessary observation.

The present invention is therefore based on the results of research conducted with a view to reducing the patients' treatment and hospitalization time and so improving their comfort by destroying targets, such as lithiases (lithotripsy) without anaesthesia.

Accordingly, it is one main object of the invention to solve the new technical problem which consists in providing a solution for treating patients with shockwaves without anesthesis.

Another object of the present invention is to solve the new technical problem consisting in providing a solution for carrying out shockwave treatments to destroy targets constituted by concretions, such as kidney lithiases or cholelithiases, such treatment being normally also known under the name of "lithotripsy", without anesthesia.

Yet another object of the invention is to solve the new technical problem consisting in providing a solution for reducing the duration of shockwave treatments in which patients would have to be kept under medical observation for only a few hours.

A further object of the present invention is to solve the new technical problem consisting in providing a solution for carrying out the treatments with shockwaves, without anesthesia, while keeping the shockwave peak pressure value to values equivalent to the peak pressure values normally used or necessary to obtain the comminution of targets and in particular concretions, such as kidney lithiases or cholelithiases, thereby ensuring an equilvalent efficiency of destruction.

All said technical problems are solved for the first time satisfactorily by the present invention.

Accordingly, a first aspect of the invention is to provide a device generating shockwaves for touchless destruction of targets, constituted for example by concretions such as kidney lithiases or cholelithiases, said shockwaves being felt only slightly, if at all, by patients, permitting a treatment without anesthesia, characterized in that is consists in manufacturing a shockwave generating device emitting shockwaves which have a mean energy density value less than about 0.23 joule/cm2 at least in one plane perpendicular to the axis of symmetry or focal axis of the emitting device, which is designed to correspond substantially to the position of the patient's skin destined to receive the shockwaves.

According to a preferred embodiment, the mean energy density of the shockwaves is between the 0.01 joule/cm2 and 0.23 joule/cm2 range, and better still, between the 0.02 joule/cm2 and 0.15 joule/cm2 range.

According to another particularly advantageous embodiment of the invention, to reduce said energy density of the shockwaves, when said shockwaves are produced by electrical discharge between at least two electrodes disposed at least partly in a chamber filled with a shockwave transmitting liquid, said electrodes being supplied intermittently with electric current from an electric current source via a current supply connection comprising a capacitor, the capacitance of said capacitor is reduced to a capacitance value lower than or equal to 500 nanofarads.

According to one advantageous embodiment, said capacitance value of the capacitor is within the 50 nanofarads and 500 nanofarads range, and better still, within the 60 and 200 nanofarads range.

According to another particularly advantageous embodiment of the invention, to reduce this mean energy density to a mean energy density unfelt by the patients, a shockwave generating ellipsoidal reflector is built so as to have a ratio of eh small diameter (b) to the large diameter (a), (b)/(a) greater than 0.60, or better still ranging between 0.60 and 0.85.

According to a particular embodiment, said ratio (b)/(a) is approximately equal to 0.64 whereas according to another particular embodiment, said ratio (b)/(a) is approximately equal to 0.75.

According to yet another particularly advantageous embodiment of the invention, reduction of said capacitance is obtained in combination with the aforesaid values of ratio (b)/(a) of the ellipsoidal reflector by way of which the shockwaves generated by the shockwave generator device are reflected. Indeed, with said combination, the shockwaves produced have assuredly a reduced energy density, which is only slightly, if at all, felt by the patient.

According to a second aspect, the invention also relates to an apparatus generating shockwaves equipped with a shockwave generating device; namely with a capacitor having the above-defined capacitance value and preferably equipped with a truncated ellipsoidal reflector having a (b)/(a) ratio as hereinabove defined.

It has been found that the invention makes it possible to generate shockwaves which are only slightly, if at all, felt by the patients, thus permitting a treatment without anesthesia.

The invention further relates to a truncated ellipsoidal reflector per se, designed so as to generate shockwaves which are only slightly, if at all, felt by the patients, characterized in that it has a (b)/(a) ratio equal to about 0.64 or to about 0.75.

A totally surprising and unexpected result of the invention resides in the fact that this reduction or elimination of feeling of the shockwaves is obtained when the peak pressure values of the shockwaves are kept to values equilvalent to the previously used peak pressure values which are necessary to destroy concretions, such as in particular kidney lithiases and cholilithiases. This constitutes an important and decisive technical improvement of the invention.

Figure 2:
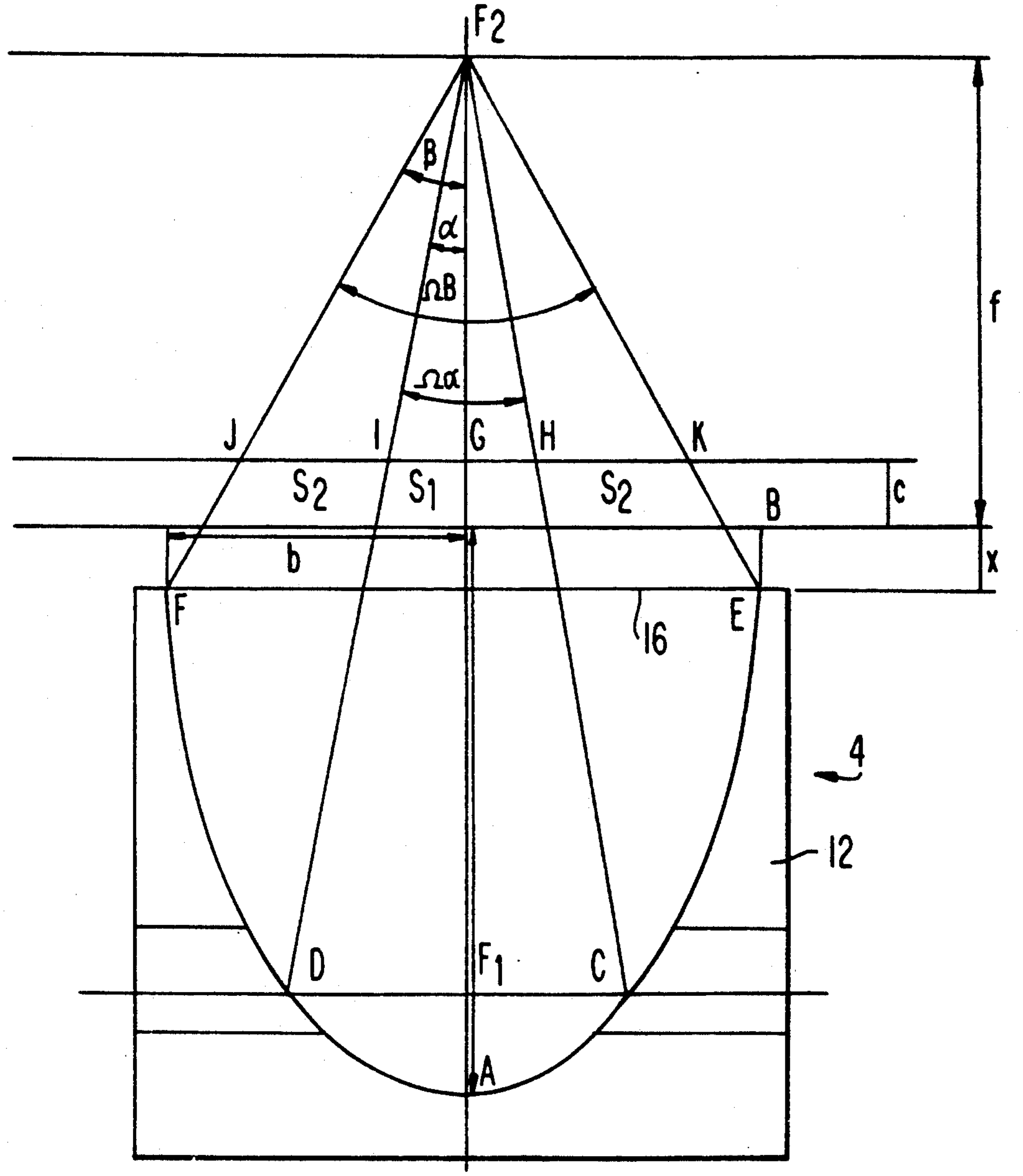

Other objects, characteristics and advantages of the invention will be more readily understood on reading the following description given with reference to the appended drawings of a currently preferred embodiment of the invention, given solely by way of example and non-restrictively. In the drawings:

FIG. 1 diagrammatically shows an ellipsoidal reflector forming part of a shockwave generating apparatus in which the main part of the connection supplying the electrodes with electric current is particularly provided with a capacitor;

FIG. 2 diagrammatically shows an axial section of a truncated ellipsoidal reflector according to the present invention.

Referring to FIGS. 1 and 2, an apparatus according to the invention for generating shockwaves in a liquid 2, such as water, for the touchless destruction of targets, for example kidney lithiases and cholelithiases, comprises a device 4 generating shockwaves by electric discharge between at least two electrodes 6, 8 situated at least partly in a chamber 10 shown here as being ellipsoid-shaped, being defined by a truncated ellipsoidal reflector 12 filled with liquid 2.

For a more detailed description of the shockwave generating device of truncated ellipsoidal shape, reference may be made to U.S. Pat. No. 2,559,227 of RIEBER or to French Patent No. 2 240 795. Reference may also be made to Applicants' prior applications FR-A-2 593 382 or FR-A-2 598 074. In particular, the electrodes 6, 8 can be mounted on an electrode advancing device such as described in prior application FR-A-2 598 074 which is incorporated herein by reference and which therefore is not described any further.

Advantageously, electrodes 6, 8 are intermittently supplied from an electric current source 22 via a connection 14 supplying electric current. Said connection 14 supplying electric current to electrodes 6, 8 is particularly provided with a capacitor 18 capable of storing a voltage of between 0 and 20,000 volts, interposed for example on the conductor 20 supplying electric current to electrode 8 from electric current source 22, combined with a high voltage transformer 24, and leading to a slide contact or to a contact nut, ensuring a permanent electrical contact with electrode 8 or with an electrode-carrier element such as described in Applicants' prior applications.

As described in particular with reference to FIG. 5 of Applicants' prior application FR-86 09 474, the supply connection 14 advantageously comprises an intermediate device 28, preferably of Spark Gap type, for intermittently breaking the electric circuit between electrodes 6, 8 interposed in the illustrated example on the other conductor 30 supplying the other electrode 6.

Conventionally, one of said conductors 20 or 30 is grounded as symbolized in FIG. 1 in T.

Said intermediate device 28 is advantageously constituted by a casing 32 in which two intermediate electrodes 34, 36 are placed at a distance from each other, said distance being sufficient to break the electric circuit.

Said electric circuit is broken by generating sparks from a spark generating device 38 such as for example a sparking plug, as used in motor vehicles or like type. To prevent premature wearing of electrodes 34, 36, it is preferably provided to scan the chamber 33 defined by casing 32 with a gaseous stream, advantageously a nitrogen stream supplied through suitable conduits 40, 42 as clearly illustrated in FIG. 1.

According to the invention, the object is to produce a device generating shockwave which are only slightly, if at all, felt by the patients, hence permitting a treatment without anesthesia. Improvements of the invention result in reducing the mean energy density of the shockwaves at least in the zone where they enter the body, namely at the level of the skin, to a mean energy density value of the shockwaves which will be only slightly, if at all, felt by the patients.

It was unexpectedly found that such mean energy density value at which the shockwaves will only slightly, if at all, be felt by the patients less than 0.23 joule/cm2.

According to the present invention, said mean energy density value is preferably reduced to a value within the 0.01 and 0.23 joule/cm2 value range, and better still within the 0.02 and 0.15 value range, particular values being approximately equal to 0.14–0.05.

Referring to FIG. 2, which shows an enlarged axial section of a truncated ellipsoidal reflector 12 according to the invention, with the electrodes 6, 8 removed, there is shown the focus F1 where the shockwaves are generated due to an electrical discharge between the electrodes 6, 8 and the second focal point F2 situated outside the truncated ellipsoidal reflector 12 and which will thereafter be brought to a position such that it coincides with the target to be destroyed, particularly a concretion such as a kidney lithiasis or cholelithiasis.

Two distinct zones of incident energy are defined on this reflector. The first zone is the lower part defined by F1 DAC, called lower zone. The other zone is the upper part defined by F1 DFEC, called upper zone. In each of these zones, 50% of the shockwave incident energy diverges from point F1. Accordingly, 50% of the energy is reflected on the wall DAC and only 30% is reflected on the wall FD and EC. The remaining 20% is lost through the opening 16 of the ellipsoidal reflector which is also defined here by the plane FE.

This figure shows a tracing of the straight line which joins up focus points F1, F2 and passes through the center of the ellipsoid 0 and which makes it possible to define the large diameter (a) defined by the segment of line OA and the small diameter (b) defined by the segment of line OB.

A point G is shown in FIG. 2, which point corresponds symbolically to the position of the patient's skin which is to undergo the shockwave treatment.

Said point G makes it possible to define a plane perpendicular to the focal axis which can be defined by the letters J, I, G, H, K. Two zones are clearly provided for focussing the shockwaves emitted at focus point F1.

The first focussing zone is defined by F2 DAC and includes the zones reflected on the wall DAC, i.e. 50% of the reflected energy.

The second zone is peripheral to the first and defined by (F2 FD) (F2 EC), therefore it constitutes an axisymmetrical zone and embodies the waves reflected on wall FD or EC, i.e. 30% of the reflected energy.

The intersection of the first zone with the plane perpendicular to the focal axis traversing point G is a circular section S1.

The intersection of the second zone with the surface in G is an annular section of surface S2.

It is found, as a result, that there is an important central energy density which is due to the high proportion of reflected energy and to the small section tranversed through.

Therefore according to the present invention, the energy density appearing mainly on the surface S1 as well as on the surface S2 is reduced, at the level of the skin, in such a way as to be below the patient's feeling threshold symbolized here by point G and by the plane perpendicular to the focal plane traversing point G, defined here by points J, I, G, H, K.

According to a first embodiment of the invention, the shockwaves mean energy density is reduced to below the mean energy density value at which the patients can feel the waves, by arranging for the discharge capacitor 18 to have a capacitance lower than or equal to 500 nanofarads.

According to a preferred embodiment, the capacitance of capacitor 18 is within a 50 nanofarads and 500 nanofarads range, and preferably within a 60 nanofarads and 200 nanofarads range.

According to another embodiment of the invention, said energy density reduction is helped by producing a truncated ellipsoidal reflector 12 whose ratio of the small diameter (b) to the large diameter (a), (b)/(a), is greater than 0.60.

According to an advantageous embodiment, said ratio (b)/(a) is between 0.60 and 0.85.

According to a particularly advantageous embodiment, ratio (b)/(a) is about equal to 0.64.

According to another particularly advantageous embodiment, said ratio (b)/(a) is about equal to 0.75.

According to a further embodiment of the invention, said capacitance values are used in combination with the ellipsoidal reflectors designed according to the invention, namely with a (b)/(a) ratio greater than 0.60, this enabling a considerable increase of the results to be obtained as well as the assured and reproducible emission of shockwaves of reduced energy density according to the invention.

All cases lead to a considerable reduction of mean energy density in the plane perpendicular to focal axis F, F2 traversing point G of FIG. 2 which is situated at approximately 100 mm of focal point F2, said reduction being concentrated substantially at skin level, and being under the threshold of energy density which is felt by the patients.

Moreover, and contrary to what might have been expected, despite a considerable reduction of the energy density, the mean pressure at focal point F2 is at least maintained, if not improved even, this allowing a smaller quantity of energy to be used.

These results are totally unexpected since anyone could have through that by reducing the total energy used, one would very quickly arrive at a pressure value which is insufficient for destroying a concretion, such as a kidney lithiasis or a cholelithiasis. But the invention has proved quite the opposite in a way completely unexpected by anyone skilled in the art.

As a result, focussing of the shockwaves is finer or more accurate. This has been proved by the experiments that were made and the results of which are given hereinafter in Tables I to III.

Table I shows the reduction of the mean energy density as a function of the shape of the ellipsoid used and of the value of the capacitance of the discharge capacitor.

It can be noted that with the previously used ellipsoid which had a ratio (b)/(a) equal to 0.57 with a capacitance 18 of 2.4 microfarads, the energy used, expressed in joule was 145, thereby giving an energy density of 0.74 joule/cm2, and a mean focussed pressure expressed in megaPascal equal to 75. Such as energy density creates a superficial hematoma, a red spot due to the shock which is often sanguinolent.

Using the same ellipsoid with a ratio (b)/(a) equal to 0.57, and reducing the capacitance to 1 microfarad and then to 0.5 microfarad (500 nanofarads), the mean energy density obtained approximately inside the plane JGK, FIG. 2, is reduced to 0.31 and then to 0.23, expressed in joule/cm2. With this last value there is no trace found on the patients although there remains a limit of feeling to shockwaves.

With an ellipsoidal reflector according to the present invention having a ratio (b)/(a) greater than 0.60, i.e. in this case 0.64 and a capacitance lower than or equal to 0.5 microfarad, in this case 0.5 and 0.2 microfarads respectively, the mean energy density obtained in joule/cm2 is respectively 0.13 and 0.05. In the first case, the mean pressure in megaPascal is 100, which is equivalent to 1,000 bars, therefore a pressure which is too high.

To obtain a mean pressure equivalent to that used previously, of about 75 megaPascal, the capacitance is reduced to a value of 0.2 microfarad, this giving no feeling at skin level and the treatment can then be carried out without anesthesia, but optionally for the patient's comfort with a slight analgesia.

The same applies when using an ellipsoid reflector according to the invention having a ratio (b)/(a) equal to 0.75 which gives a mean energy density equal to 0.04. It is to be noted that such ellipsoidal reflector has an added unexpected advantage which is an improved distribution of the energy (energy density) on the flux of reflected wave outputted by the reflector.

It should be noted that the pressure value is measured with a pressure sensor of reference PCB119A02 whose own frequency is 500 kH. Said pressure sensor filters the shockwave building-up times and delivers a constant value of 500 nanoseconds. It can also filter the decrease of the wave to a value of 500 nanoseconds.

The measured energy density is a mean energy density which is obtained by working out the mean value of the energy density values obtained as a function of the distances. Said energy density is obtained from the peak pressure measured (PP). The distribution of the focussed peak pressures is in fact given in Table II below, inside plane J, G, K perpendicular to the focal axis as a function of the distance Y expressed in millimeters from the focal plane. It has been found that a high energy density zone is situated in the zone of focal axis F1F2 (y=0), the energy reducing as the sensor moves along a radial axis outwardly from the reflector.

Finally, Table III hereafter shows the practical values for the construction of an ellipsoidal reflector, whether according to the prior art (No. 1) with ratio (b)/(a) equal to 0.57, or according to the invention (No. 2) with a ratio (b)/(a) equal to 0.64, or according to a second embodiment of the invention (No. 3) with a ratio (b)/(a) equal to 0.75. The energy density values are calculated in consideration that the shockwave is created in one point of focus F1, by applying a reflection coefficient of the metal, in this case brass, of 0.80, on the basis of the energy stored by the capacitor and by taking into account the losses non-reflected on the ellipsoid (11 to 23%).

The Table shows the percentage of reflected energy (RE), angle $\alpha$ is the angle DF2A shown in FIG. 2 and $\beta$ is the angle FF2A shown in FIG. 2. The result is solid angle $\Omega\alpha$ defined by DF2C revolving around axis F1F2, and called an internal solid angle. Moreover, angle $\beta$ gives solid angle $\Omega\beta$ defined by FF2E revolving around axis F1F2. There is thus obtained the external solid angle of reflection defined by the external solid angle of revolution FF2BCF2B $\Omega$ equal to $\Omega\beta$ less $\Omega\alpha$, as well as the respectively internal and external energetic coefficients defined in Table III.

It is thus found that the invention makes it possible to considerably reduce the internal energetic coefficient, thus leading to a reduction of the energy density according to the invention. A value of 227 is indeed obtained for the ellipsoidal reflector according to the invention having a ratio (b)/(a) equal to 0.64 compared to a coefficient of 417 for an ellipsoidal reflector according to the prior art having a ratio (b)/(a) equal to 0.57, i.e. a reduction of virtually 50%.

Another reduction of about 50% is obtained by selecting the ellipsoidal reflector according to the invention having a (b)/(a) ratio equal to 0.75, while maintaining an external energetic coefficient virtually similar to that of the ellipsoidal reflector according to the invention having a ratio (b)/(a) equal to 0.64.

Owing to the invention which reduces considerably the energy density, at least at skin level, patients hardly feel the created shocks, hence the possibility of treating them virtually without anaesthesia. It is sufficient to apply to them just a slight analgesia throughout the treatment, in order to make them more comfortable.

On the other hand, identical pressure values have been kept in order to obtain the destruction of concretions with the same efficiency.

Another completely unexpected advantage of the invention resides in the fact that by altering the shape of the ellipsoidal reflector so that its ratio (b)/(a) is greater than 0.60, a finer focus spot is obtained with, therefore, an improved concentration of energy at external focal point F2, this further reducing the risks of tissues being destroyed around the target to be destroyed, whether this target is a tissue or a concretion, by improving the accuracy of the shots.

It is worth noting that the frequency spectrum is composed of high frequency components due to the short building-up time of the wave and of low frequency components due to a return of the wave to a balanced state with a very high time constant, given the wave building-up time.

The building-up times with PVDF sensors are about 200 ns. The time constants are in the region of 1 $\mu$s.

The low frequency components are very energetic and seem to be strongly felt by the patients when the wave time constant is high than 1.5 $\mu$s.

Moreover, according to the invention, the shockwaves have a high frequency higher than 300 kH whereas the shockwaves according to the prior art which have a low frequency and a high energy density, cause skin lesions, as clearly shown in Table I hereunder.

The invention of course covers all the means constituting technical equivalents of the means described herein as well as the various combinations thereof.

Accordingly, the expression "shockwaves slightly, if at all, felt at skin level by the patients" should be understood to mean shockwaves which, although they can be felt by the patient, are bearable and do not necessitate any anesthesia, a mere analgesia throughout the treatment being sufficient to improve the patient's comfort.

Anyone skilled in the art will of course understand clearly the reach of this expression, particularly in view of the energy density values given in the present description including the Tables and the figures which form an integral part of the invention.

TABLE I

| | Reduction of the energy density as a function of the shape of the ellipsoid and of the value of the capacitance of the discharge capacitor | | | | | | | | |
|---|---|---|---|---|---|---|---|---|---|
| | Ellipsoid ratio b/a | Capacity $\mu$F | Frequency KHz | Reactor nH | Energy Joule | Energy density ED. J/cm$^2$ | Mean pressure (MPa) | Time $\mu$s | Remarks on patient's treatments |
| Prior Art | 0.57 | 2.4 | 125 | 675 | 145 | 0.74 | 75 | 0.9 | Creation of superficial bruise red spot (hit spot) often sanguinolent |

TABLE I-continued

Reduction of the energy density as a function of the shape of the ellipsoid and of the value of the capacitance of the discharge capacitor

| | Ellipsoid ratio b/a | Capacity μF | Frequency KHz | Reactor nH | Energy Joule | Energy density ED. J/cm² | Mean pressure (MPa) | Time μs | Remarks on patient's treatments |
|---|---|---|---|---|---|---|---|---|---|
| Prior Art | 0.57 | 1 | 193 | 680 | 61 | 0.31 | 80 | 0.6 | Red sanguinolent central spot of several cm in diameter and slight redness on the periphery. The central spot corresponds to a zone of high energy density and in particular to the reflecting zone on the bottom of the reflector. |
| Modified Prior Art | 0.57 | 0.5 | 288 | 610 | 45 | 0.23 | 75 | 0.5 | No traces are noted on the patient's, patient's feeling of shock waves restricted. |
| Invention | 0.64 | 0.5 | 353 | 551 | 42 | 0.13 | 100 | | Change of characteristic of reflector. Increase of outgoing surface. Measured pressure too high. |
| Invention | 0.64 | 0.2 | 500 | 507 | 17 | 0.05 | 76 | 0.5 | Treatment with slight analgesia |
| Invention | 0.75 | 0.2 | 500 | 520 | 17 | 0.04 | | | Treatment with slight analgesia |

E = 0.5 CU2
U supply voltage (Volt)
C Capacitance (Farad)
E Energy in Joules

TABLE II

Distribution of peak pressures focussed in a plane perpendicular to the focal axis. (parameters defined in FIG. 1 and Table III) Ellipsoid 0.64 C = 50 mm

| Ymm | 0 | 10 | 20 | 30 | 40 | 50 |
|---|---|---|---|---|---|---|
| Relative PP | 1 | 0.93 | 0.37 | 0.12 | 0.1 | 0.06 |
| Relative ED | 1 | 0.86 | 0.14 | 0.014 | 0.010 | 0.004 |

Mean maximum peak pressure: 22.9 MPa (229 bars)
Measuring conditions:
Frequency 444 KHz
Capacitance 200 nF
Inductance 640 nH

TABLE III

Ellipsoidal shape and energy density (parameters defined in FIG. 2)

| Ellipsoid b/a | a | b | f | x | Reflected energy ($R_E$) % | α | β | $\Omega_\alpha$ | Ω ext. $\Omega_\beta - \Omega_\alpha$ | *50 / $\Omega_\alpha$ | **100 $R_E$ − 50 / Ω ext. |
|---|---|---|---|---|---|---|---|---|---|---|---|
| 1 (0.57) (prior art) | 140 | 80 | 114.9 | 15.1 | 89 | 11°.25 | 31°.25 | 0.12 | 0.8 | 417 | 49 |
| 2 (0.64) Invention | 190.1 | 109.8 | 130 | 0 | 88 | 15°.23 | 40°.17 | 0.22 | 0.26 | 227 | 30 |
| 3 (0.75) Invention | 150.2 | 112 | 100 | 30 | 77 | 22°67 | 40°.17 | 0.49 | 0.99 | 102 | 27.3 |

*Internal energetic coefficient
**External energetic coefficient

We claim:

1. Apparatus for destruction of a target in the body of a subject, comprising:

means for generating shock waves;

means for focusing said shock waves on said target, said shock waves passing through a plane adjacent said body, said plane being intermediate said body and said means for generating shock waves;

said focusing means comprises a truncated ellipsoidal reflector having a first focal point therein and a second focal point external thereto and coincident with said target; said shock wave generating means comprising means for generating shock waves of a predetermined power including a pair of electrodes spaced on either side of said first focal point and an electric current supply circuit comprising a capacitor connected to said electrodes for generating an electrical discharge therebetween; and wherein the mean electrical energy density, which comprises the electrical energy of said discharge divided by the effective surface area of said shock waves substantially at said plane, is less than about 0.23 joule/cm².

2. The apparatus of claim 1, wherein said capacitor has a capacitance less than or equal to 500 nanofarads.

3. The apparatus of claim 2, wherein said capacitor has a capacitance in a range from 50 nanofarads to 500 nanofarads.

4. The apparatus of claim 3, wherein said capacitor has a capacitance in a range from 60 nanofarads to 200 nanofarads.

5. The apparatus of claim 4, wherein said truncated ellipsoidal reflector has a ratio (b)/(a) of its small diameter (b) to its large diameter (a) greater than about 0.60.

6. The apparatus of claim 5, wherein said ratio is in the range of 0.60 to 0.85.

7. The apparatus of claim 6, wherein said ratio is about 0.64 or about 0.75.

8. The apparatus of claim 2, wherein said truncated ellipsoidal reflector has a ratio (b)/(a) of its small diameter (b) to its large diameter (a) greater than 0.60.

9. The apparatus of claim 8, wherein said ratio is in the range of from 0.60 to 0.85.

10. The apparatus of claim 9, wherein said ratio is about 0.64 or about 0.75.

11. The apparatus according to claim 1, wherein said predetermined power of said means for generating shock waves and said predetermined geometry of said means for focusing said shock waves comprises means for generating shock waves having a mean electrical energy density at said plane of from 0.01 joules/$cm^2$ to 0.23 joules/$cm^2$.

12. The apparatus according to claim 11, wherein said predetermined power of said means for generating shock waves and said predetermined geometry of said truncated ellipsoidal reflector comprises means for generating shock waves having an electrical energy density at said plane of from 0.02 joules/$cm^2$ to 0.15 joules/$cm^2$.

13. The apparatus according to claim 12, wherein said truncated ellipsoidal reflector has a ratio (b)/(a) of its small diameter (b) to its large diameter (a) greater than about 0.60.

14. The apparatus according to claim 13, wherein said ratio is in the range of 0.60 to 0.85.

15. The apparatus according to claim 14, wherein said ratio is about 0.64 or about 0.75.

16. A method for destroying a target in a body comprising:

generating shock waves having a predetermined power;

focusing said shock waves on said target in the body, said shock waves passing through a plane adjacent the body, said plane being intermediate said target and said means for generating shock waves; and selecting said predetermined power and focusing said shock waves on said target such that the mean electrical energy density of the shock waves at said plane corresponds to the mean energy density produced by: a focusing means comprising a truncated ellipsoidal reflector having a first focal point therein and a second focal point external thereto and coincident with said target; a shock wave generating means comprising a pair of electrodes spaced on either side of said first focal point and an electric current supply circuit comprising a capacitor connected to said electrodes for generating an electrical discharge therebetween; and wherein the mean electrical energy density, comprising the electrical energy of said discharge divided by the effective surface area of said shock wave substantially at said plane, is less than about 0.23 joule/$me^2$.

17. The method of claim 16, wherein said step of generating shock waves comprises generating shock waves between said pair of electrodes spaced on either side of said first focal point and providing said electric circuit including said capacitor having a capacitance less than or equal to or about 500 nanofarads for supplying electric current to said electrodes.

18. The method of claim 17, wherein said step of providing said capacitor comprises providing a capacitor having a capacitance in the range of from 50 nanofarads to 500 nanofarads.

19. The method of claim 18, wherein said step of providing said capacitor comprises providing a capacitor with a capacitance in a range of from 60 nanofarads to 200 nanofarads.

20. The method of claim 19, wherein said step of providing said truncated ellipsoidal reflector comprises providing a truncated ellipsoidal reflector having a ratio of its small diameter (b) to its large diameter (a) of greater than 0.60.

21. The method of claim 20, wherein said step of providing said truncated ellipsoidal reflector comprises providing a truncated ellipsoidal reflector having a ratio of its small diameter (b) to its large diameter (a) in the range of 0.60 to 0.85.

22. The method of claim 17, wherein said step of providing said truncated ellipsoidal reflector comprises providing a truncated ellipsoidal reflector having a ratio of its small diameter (b) to its large diameter (a) of greater than about 0.60.

23. The method of claim 16, wherein said step of providing said truncated ellipsoidal reflector comprises providing a truncated ellipsoidal reflector having a ratio of its small diameter (b) to its large diameter (a) of greater than 0.60.

24. The method of claim 23, wherein said step of providing said truncated ellipsoidal reflector comprises providing a truncated ellipsoidal reflector having a ratio of its small diameter (b) to its large diameter (a) in the range of 0.60 to 0.85.

25. The method of claim 24, wherein said step of providing said truncated ellipsoidal reflector comprises providing a truncated ellipsoidal reflector having a ratio of its small diameter (b) to its large diameter (a) is about 0.64 or about 0.75.

26. The method of claim 16, wherein said step of selecting said predetermined power and focusing said shock waves on said target comprises selecting said predetermined power and focusing said shock waves on said target such that the mean electrical energy density of the shock waves at said plane is in a range from 0.01 joules/$cm^2$ to 0.23 joules/$cm^2$.

27. The method of claim 26, wherein said step of selecting said predetermined power and focusing such said shock waves on said target comprises selecting predetermined power and focusing said shock waves on said target such that the mean electrical energy density of the shock waves at said plane is in a range from 0.02 joules/$cm^2$ to 0.15 joules/$cm^2$.

28. The method of claim 26, wherein said step of providing said truncated ellipsoidal reflector comprises providing a truncated ellipsoidal reflector having a ratio of its small diameter (b) to its large diameter in the range of 0.60 to 0.85.

29. The method of claim 28, wherein said step of providing said truncated ellipsoidal reflector comprises providing a truncated ellipsoidal reflector having a ratio of its small diameter (b) to its large diameter (a) of about 0.64 or about 0.75.

30. The method of claim 26, wherein said step of selecting said predetermined power and focusing such said shock waves on said target comprises selecting said predetermined power and focusing said shock waves on said target such that the mean electrical energy density of the shock waves at said plane is in a range from 0.02 joules/$cm^2$ to 0.15 joules/$cm^2$.

31. The method of claim 30, wherein said step of providing said truncated ellipsoidal reflector comprises providing a truncated ellipsoidal reflector having a ratio of its small diameter (b) to its large diameter (a) of greater than 0.60.

32. The method of claim 31, wherein said step of providing said truncated ellipsoidal reflector comprises providing a truncated ellipsoidal reflector having a ratio of its small diameter (b) to its large diameter (a) in the range of 0.60 to 0.85.

33. The method of claim 32, wherein said step of providing said truncated ellipsoidal reflector comprises providing a truncated ellipsoidal reflector having a ratio of its small diameter (b) to its large diameter (a) of about 0.64 or about 0.75.

34. The method of claim 16, wherein said step of focusing said shockwaves on said target in the body comprises focusing said shockwaves on a kidney lithiase or a cholelithiase.

35. The method of claim 16, wherein the destruction of said target in the body is performed without the administration of an anesthesia to said body.

* * * * *